(12) United States Patent
McHugo (10) Patent No.: US 8,709,063 B2
(45) Date of Patent: Apr. 29, 2014

(54) BIFURCATED STENT INTRODUCER SYSTEM

(75) Inventor: Vincent McHugo, Birdhill (IE)

(73) Assignee: Cook Medical Technologies LLC, Bloomington, IN (US)

( * ) Notice: Subject to any disclaimer, the term of this patent is extended or adjusted under 35 U.S.C. 154(b) by 183 days.

(21) Appl. No.: 13/160,640

(22) Filed: Jun. 15, 2011

(65) Prior Publication Data

US 2011/0313505 A1 Dec. 22, 2011

Related U.S. Application Data

(60) Provisional application No. 61/356,288, filed on Jun. 18, 2010.

(51) Int. Cl.
*A61F 2/06* (2013.01)

(52) U.S. Cl.
USPC .......................................... 623/1.12; 623/1.35

(58) Field of Classification Search
USPC ..................... 623/1.11, 1.12, 1.35, 1.16, 1.23
See application file for complete search history.

(56) References Cited

U.S. PATENT DOCUMENTS

| 6,099,548 | A | 8/2000 | Taheri |
| 7,537,606 | B2 | 5/2009 | Hartley et al. |
| 2008/0114437 | A1 | 5/2008 | Ozhered et al. |
| 2008/0221668 | A1 | 9/2008 | Pinchuk et al. |
| 2008/0262592 | A1 | 10/2008 | Jordan et al. |
| 2009/0099640 | A1 | 4/2009 | Weng |

FOREIGN PATENT DOCUMENTS

| WO | WO 96/36269 A2 | 11/1996 | |
| WO | WO 00/13613 A1 | 3/2000 | |
| WO | WO 2008/098255 | * 8/2008 | ............ A61M 25/08 |

OTHER PUBLICATIONS

International Search Report mailed Sep. 5, 2011 for International Application No. PCT/US2011/040431.
Written Opinion mailed Sep. 5, 2011 for International Application No. PCT/US2011/040431.

* cited by examiner

*Primary Examiner* — Thomas McEvoy
(74) *Attorney, Agent, or Firm* — Brinks Gilson & Lione (57) ABSTRACT

A stent delivery system and a method for implanting a stent are provided. The system includes first and second elongate shafts, each shaft including a proximal portion, a distal portion, and a lumen extending at least partially therethrough. The second shaft is longitudinally movable relative to the first shaft. The system also includes a bifurcated stent having a first arm positioned on the first shaft and a second arm positioned on the elongate shaft and a main body positioned on the first and second shafts. Proximal and first and second distal constraining members are releasably connected to the stent. The proximal and the first and second distal constraining members cooperatively apply longitudinal tensile force to at least a portion of the stent with the proximal and first and second distal constraining members each in the first position.

12 Claims, 9 Drawing Sheets

BIFURCATED STENT INTRODUCER SYSTEM

RELATED APPLICATIONS

This application claims the benefit of U.S. Provisional Application No. 61/356,288, filed Jun. 18, 2010, which is incorporated by reference herein in its entirety.

TECHNICAL FIELD

This invention relates to a medical device and, in particular to a device for delivering and deploying a bifurcated stent and a method of delivering and deploying the stent into a body lumen.

BACKGROUND

A self-expanding stent is typically introduced into the body using a delivery device that includes an outer sheath coaxially disposed and slidable over an inner catheter to hold the stent in a low profile configuration for delivery to a treatment site. The stent is disposed at the distal end of the device between the inner catheter and the outer sheath and held in a compressed position by the outer sheath. The stent is held in the compressed position and guided through a bodily lumen to the treatment site. Once the delivery system and the stent are adjacent to the treatment site, the stent may be deployed by proximally pulling back the outer sheath relative to the inner catheter until the stent is exposed. The self-expanding stent expands from the stent distal end to the stent proximal end as the sheath is proximally withdrawn. The delivery system may include a step or other feature is provided on the inner catheter to prevent the stent from moving rearward with the outer sheath when the outer sheath is withdrawn. Some delivery devices for self-expanding stents include a trigger wire to hold the stent in position while the outer sheath is withdrawn.

As the stent is released from the outer sheath, the stent springs radially outward to an expanded diameter until the stent contacts and presses against the vessel wall. When a trigger wire is present, the trigger wire is released and the stent expands outwardly at the treatment site. Distally withdrawing the outer sheath may cause difficulty in accurately placing the proximal portion of the stent because the distal end of the stent is positioned first while the proximal portion of the stent is still covered by the outer sheath. Releasing the trigger wire from the stent at the ends allows the stent to expand and completely releases the stent from the delivery system. However, if the trigger wires are released and the stent expands into an improper position, the stent cannot be repositioned.

Similar delivery devices may also be used for delivering one or more stents to a bifurcation in a vessel. The stent may be positioned in one or more branches of the bifurcation to treat a lesion at the bifurcation. Delivery of a bifurcated stent to the treatment site in the desired position may be difficult. For example, expansion of a bifurcated stent requires non-uniform expansion forces in the main body and the branches of the stent. Release of a bifurcated stent from the delivery system by withdrawal of the outer sheath can result in improper placement of the bifurcated stent due to the non-uniform expansion of the stent when the stent is released. Similarly, release of the bifurcated stent from the trigger wires can result in improper positioning of a portion of the stent within the bifurcation.

Accordingly, in view of the drawbacks of current technology, there is a desire for a delivery system that can increase the control, accuracy and ease of placement of a bifurcated stent during deployment of the bifurcated stent within a patient. The delivery system would ideally reduce the risk of malfunction while providing for a smoother, more accurate and quicker deployment of the entire stent. The delivery system also would provide the ability to reconstrain, recapture, reposition and/or remove the bifurcated stent after expansion of the stent.

SUMMARY OF THE INVENTION

Accordingly, it is an object of the present invention to provide a device and a method having features that resolve or improve on one or more of the above-described drawbacks.

The foregoing object is obtained in one aspect of the present invention by providing a stent delivery system. The stent delivery system includes a first elongate shaft including a proximal portion, a distal portion, a lumen extending at least partially therethrough, and a second elongate shaft including a proximal portion, a distal portion, an a lumen extending at least partially therethrough. The second elongate shaft is longitudinally movable relative to the first elongate shaft. The stent delivery system also includes a bifurcated stent having a first arm positioned on the first elongate shaft and a second arm positioned on the second elongate shaft and a main body position on the first and second elongate shafts. A proximal constraining member and first and second distal constraining member releasably connected to the stent and having a first position and a second position are also included. The proximal constraining member and the first and second distal constraining members cooperatively apply longitudinal tensile force to at least a portion of the stent with the proximal and first and second distal constraining members each in the first position.

In another aspect of the present invention, a method for implanting a stent using a stent delivery system is provided. The method includes inserting a distal portion of a stent delivery system into the lumen of a patient. The stent delivery system includes a first and second elongate shaft each including a proximal portion, a distal portion, and a lumen extending at least partially therethrough. The stent delivery system also includes a bifurcated stent having a first arm positioned on the first elongate shaft and a second arm positioned on the second elongate shaft and a main body position on the first and second elongate shafts. A proximal constraining member and first and second distal constraining member releasably connected to the stent and having a first position and a second position are also included. The method further includes holding the stent in the constrained configuration with a longitudinal tensile force applied to the stent by the proximal and first and second distal constraining members each in the first position and cooperatively tensioning the stent for delivery of the stent to the implant site, positioning the stent at the implant site and expanding the stent to the expanded configuration by moving the proximal and first and second distal constraining members each to the second position and releasing longitudinal tensile force on the stent.

In another aspect of the present invention, a method of implanting a bifurcated stent in a patient's lumen. The method includes inserting a distal portion of a stent delivery system into the lumen of a patient and holding the stent in a constrained configuration for delivery of the stent to the implant site. The method further includes positioning the stent at the implant site so that a first arm of the stent is positioned at least partially in a first lumen and a second arm of the stent is at least partially positioned in a second lumen and expanding the stent to the expanded configuration after the stent is positioned in the first and second lumens by moving the delivery system to a second position and unconstraining the stent.

DETAILED DESCRIPTION OF THE EMBODIMENTS

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the stent to a patient. Hence the term "distal" means the portion of the delivery system that is farthest from the physician and the term "proximal" means the portion of the delivery system that is nearest to the physician.

Figure 1:
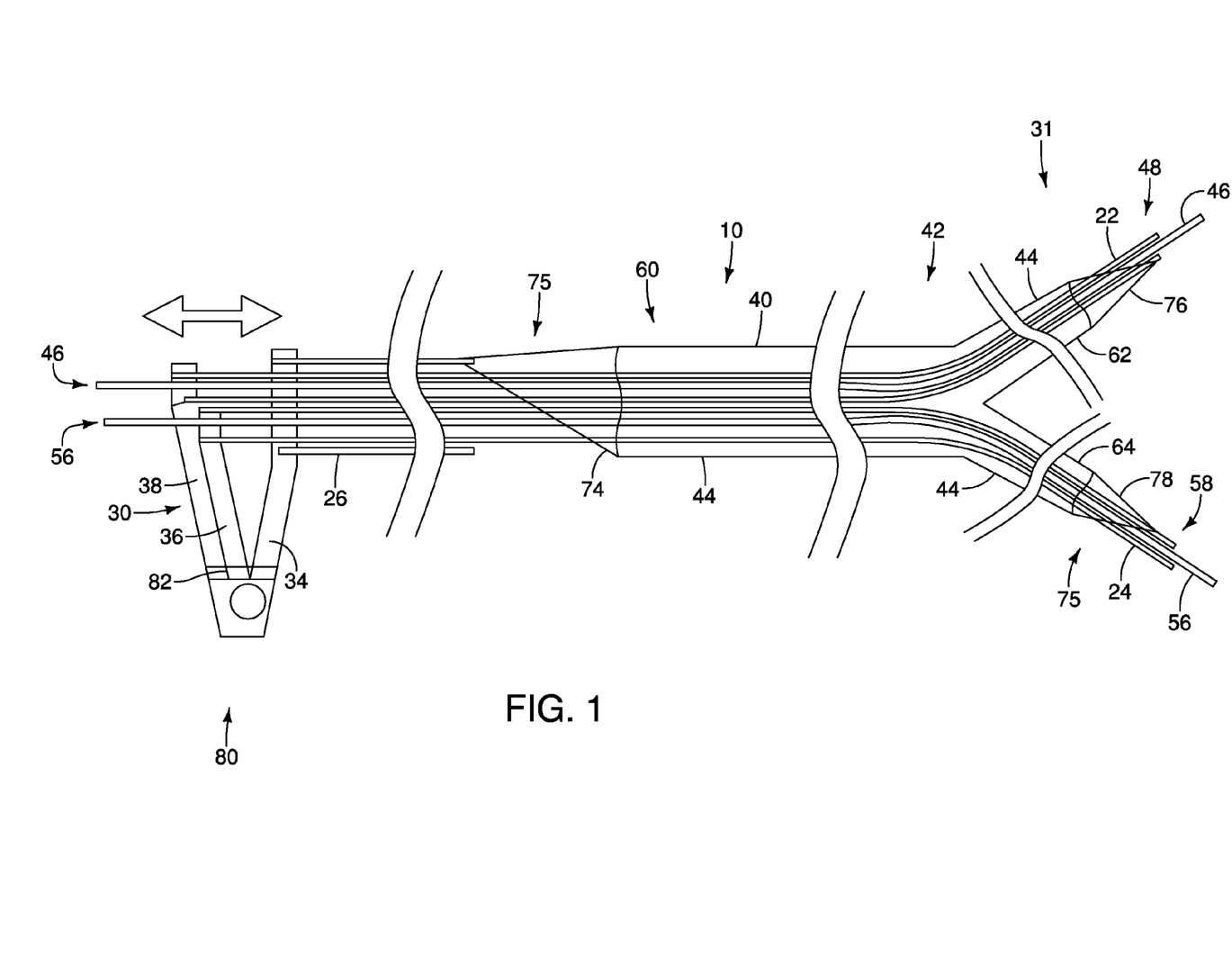
FIG. 1 is a side view of a stent delivery system according to an embodiment of the present invention.

FIG. 1 illustrates a stent delivery system 10 for in accordance with embodiments of the present invention. The stent delivery system 10 includes a first inner shaft 22, a second inner shaft 24 and an outer shaft 26. The stent delivery system 10 further includes a handle 30 at a proximal portion 32 of the system 10. The handle 30 includes a distal arm 34 operably connected to the outer shaft 26, a first proximal arm 36 connected to the first inner shaft 22 and a second proximal arm 38 operably connected the second inner shaft 24. A bifurcated stent 40 is positioned on a distal portion 42 of the delivery system 10. One or more radiopaque markers 44 may be included on the delivery system 10 to indicate the position of the stent 28. The stent delivery system 10 may also include a first guidewire 46 extendable through the first inner shaft 22 through a first distal tip 48 at the distal portion 42 of the delivery system 10. The stent delivery system 10 may also include a second guidewire 56 extendable through the second inner shaft 24 through a second distal tip 58 at the distal portion 44 of the delivery system 10.

Figure 2:
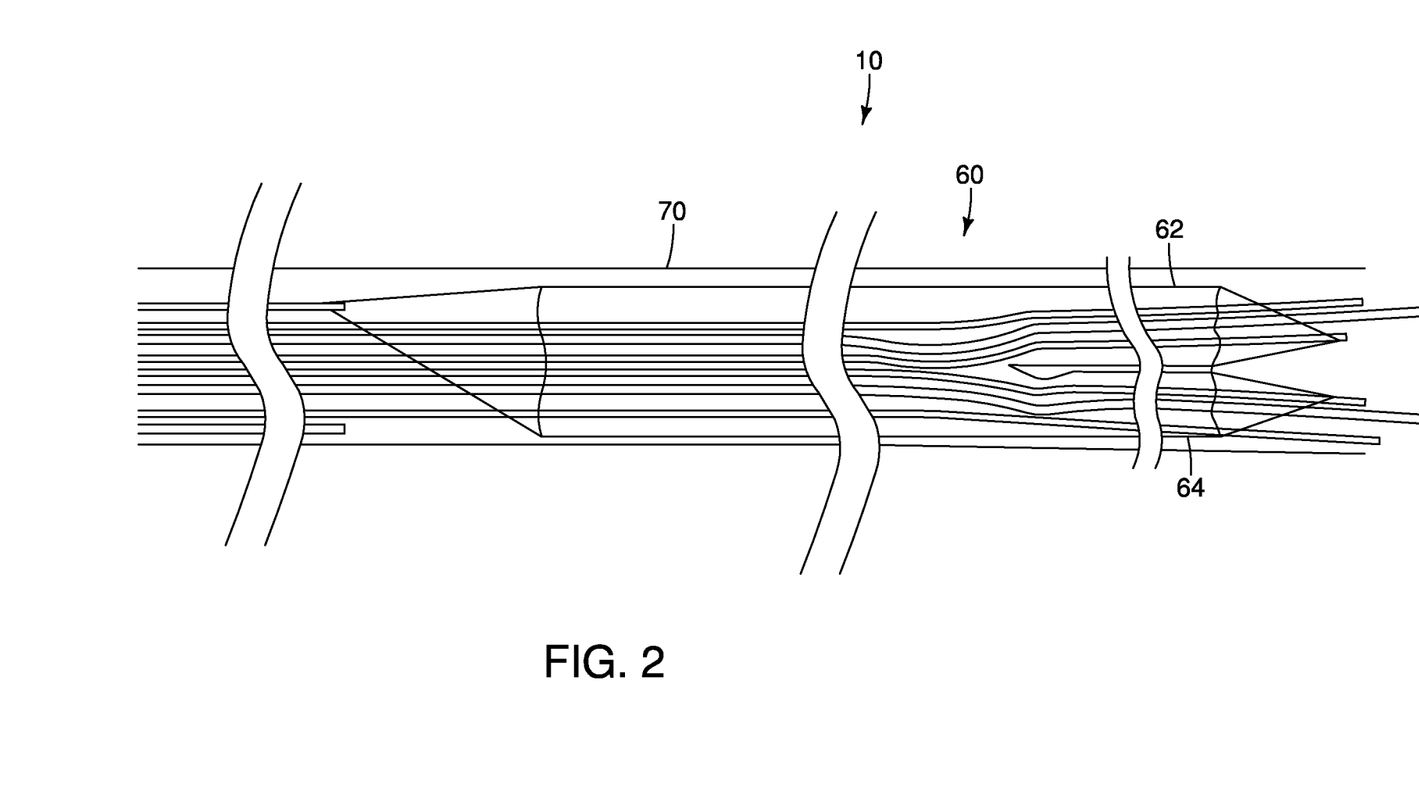
FIG. 2 is a partial side view of the device shown in FIG. 1 showing the stent in a constrained configuration and having a sheath.

As shown in FIG. 1, the bifurcated stent 40 is in a constrained configuration 60 collapsed against the first inner shaft 22 and the second inner shaft 24. The bifurcated stent 40 shown in FIG. 1 illustrates a first stent arm 62 and a second stent arm 64 shown spaced apart for clarity. For initial delivery to the treatment site, the first and second stent arms 62, 64 can be collapsed closer together as shown in FIG. 2. An outer sheath 70 may also be provided in some embodiments. As shown in FIG. 2, the outer sheath 70 is positioned over the bifurcated stent 40 in the constrained configuration 60 and may be used to facilitate delivery of the bifurcated stent 40 to the treatment site.

Figure 3:
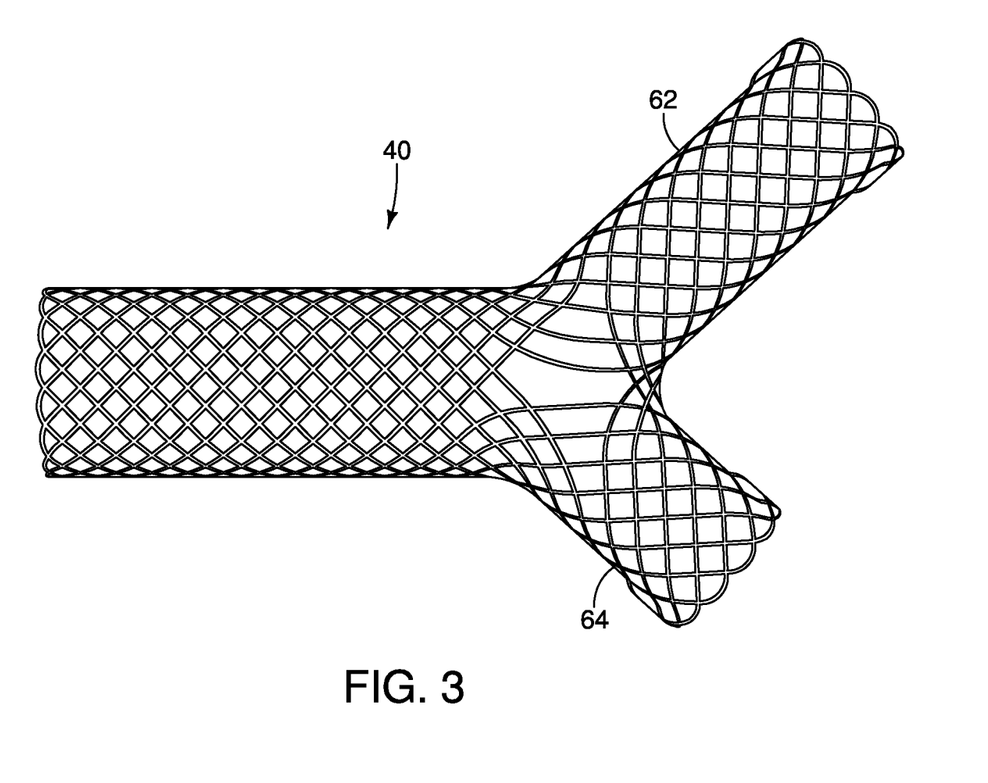
FIG. 3 is a side view of an exemplary bifurcated stent deliverable using the stent delivery system.

In some embodiments, the bifurcated stent 40 may be a self-expanding stent. The stent 40 may be any kind of stent that has a tendency to radially collapse when a longitudinal force is applied to the ends of the stent. By way of non-limiting example, the stent 40 may be formed as a woven mesh formed from a metal or polymer or a laser cut pattern formed in a metal stent where the bifurcated stent is provided as a unitary stent. The stent may also be formed from a bioabsorbable material. An exemplary bifurcated stent that may be delivered using the delivery system 10 is shown in FIG. 3. (Available from Micro-Tech China.)

The stent 40 is held in the constrained configuration 60 by a proximal stent constraining member 74 and a first distal stent constraining member 76 and a second distal stent constraining member 78 to longitudinally constrain the stent 40 and hold the stent 40 collapsed against the first and second inner shafts 22, 24 as shown in FIG. 1. The constraining members are discussed in more detail below with reference to FIGS. 6A-6C and 7-10. The proximal, first and second distal stent constraining members 74, 76, 78 are shown in a first position 75 constraining the stent 40 in a tensioned configuration against the first and second inner shafts 22, 24. The proximal, first and second distal stent constraining members 74, 76, 78 are operably connected to the handle 30 by connection of the proximal constraining member 74 to the outer catheter 26 and the first distal constraining member 76 to the first inner shaft 22 and the second distal constraining member 78 to the second inner shaft 24. As described below, the first and second inner shafts 22, 24 may be independently movable. When present, the outer sheath 70 may provide some compressive force to the stent 40 in addition to the proximal, first and second distal constraining members 74, 76, 78. The handle 30 is shown FIG. 1 in a closed position 80. The handle 30 may include a lock 82 to releasably lock the handle 30 in the closed position 80, for example, for delivery of the stent 40 to the treatment site.

Figure 4:
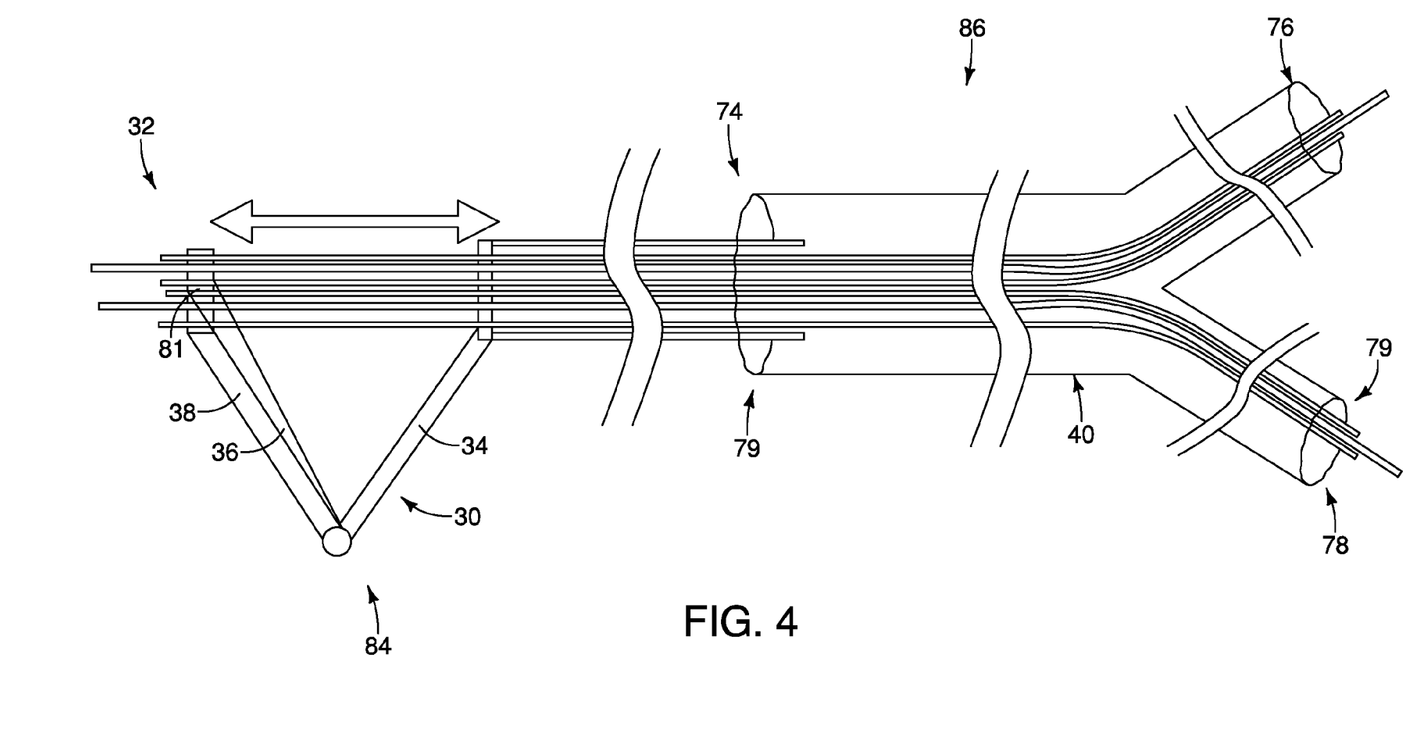
FIG. 4 is a side view of the device shown in FIG. 1 with the stent in an expanded configuration.

As shown in FIG. 4, the bifurcated stent 40 is in an expanded configuration 86 where the bifurcated stent 40 is expanded away from the first inner shaft 22 and the second inner shaft 24. The proximal and first and second distal constraining members 74, 76, 78 are in a second position 79 and remain connected to the stent 40 but the longitudinal force on the bifurcated stent 40 has been removed to allow the stent 40 to expand. The handle 30 has been moved to an open position 84 by expanding first and second proximal arms 36 and 38 away from distal arm 34 of the handle 30. In some embodiments, the arms 36 and 38 are expanded in equal and opposite directions in relation to the arm 34. When the handle arms 36, 38 and 34 are moved apart from each other, the proximal constraining member 74 is moved closer to the first and second distal constraining members 76, 78 and the tension on the bifurcated stent 40 is released. The first and second proximal arms 36, 38 may be removably connected by a handle lock 81 when the first and second stent arms 62, 64 are to be expanded at the same time.

As shown in FIG. 4, the proximal and first and second distal constraining members 74, 76, 78 remain connected to the bifurcated stent 40 in the expanded configuration 86. The connection allows the bifurcated stent 40 to be moved from the expanded configuration 86 to the constrained configuration 60 so that the bifurcated stent 40 is recollapsed onto the first and second inner shafts 22, 24 by handle 30 to the closed position 80. The handle 30 moves the first and second inner shafts 22, 24 and the outer catheter 26 relative to each other so that the proximal and first and second distal constraining members 74, 76, 78 are spaced further apart and the longitudinal tension is returned to the stent 40 to collapse the stent onto the first and second inner shafts 22, 24. The bifurcated stent 40 may be repeatedly moved between the constrained configuration 60 and the expanded configuration 86 by moving the handle 30 between the closed position 80 and the open position 84 until the bifurcated stent 40 is properly positioned. The stent configurations may be changed multiple times within the patient for repositioning or removal until the proximal and first and second distal constraining members 74, 76, 78 are released from connection with the stent 40 as described below.

Figure 5:
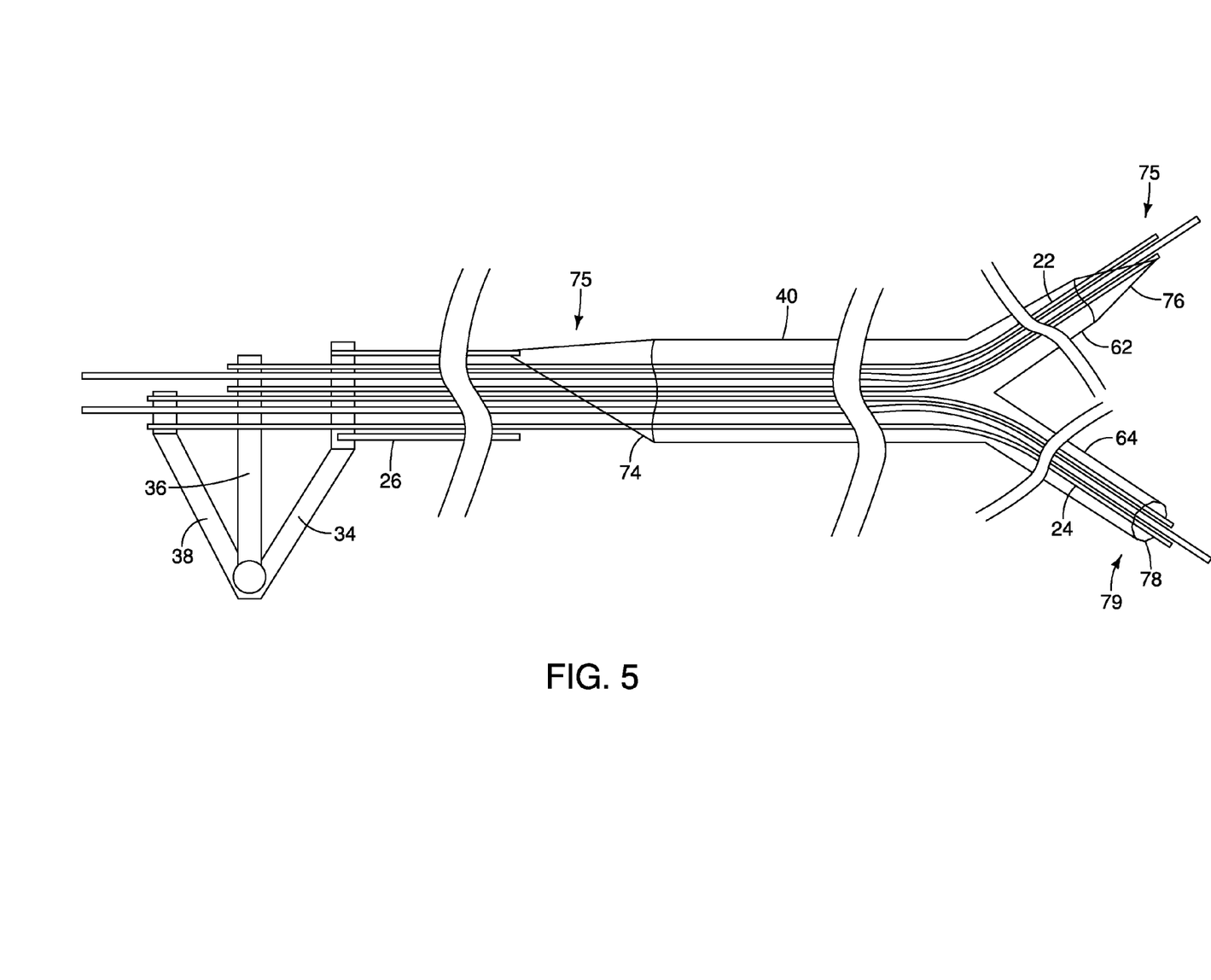
FIG. 5 is a side view of the device shown in FIG. 1 with one arm of the stent in an expanded configuration.

As shown in FIG. 5, the first and second proximal arms 36, 38 may be moved separately with respect to each other to expand one of the first or second stent arms 62, 64 while the other of the first or second stent arm 62, 64 remains constrained. FIG. 5 illustrates the second stent arm 64 with the second distal constraining member 78 in the second position 79. The second proximal arm 38 of the handle 30 has been moved proximally which also proximally moves the second inner shaft 24 relative to the outer shaft 26. The tension on the second stent arm 64 is released and the second stent arm 64 expands away from the second inner shaft 24. Expanding one stent arm while leaving the other stent arm constrained may facilitate placement of the bifurcated stent 40 in the bifurcated target site. The second stent arm 64 may be reconstrained by moving the second proximal arm 38 of the handle 30 back to the closed position and moving the proximal and second distal constraining members 74, 78 further apart to re-tension the bifurcated stent 40. As will be understood by one skilled in the art, the first stent arm 62 may also be expanded while the second stent arm 64 remains constrained.

Figure 6A:
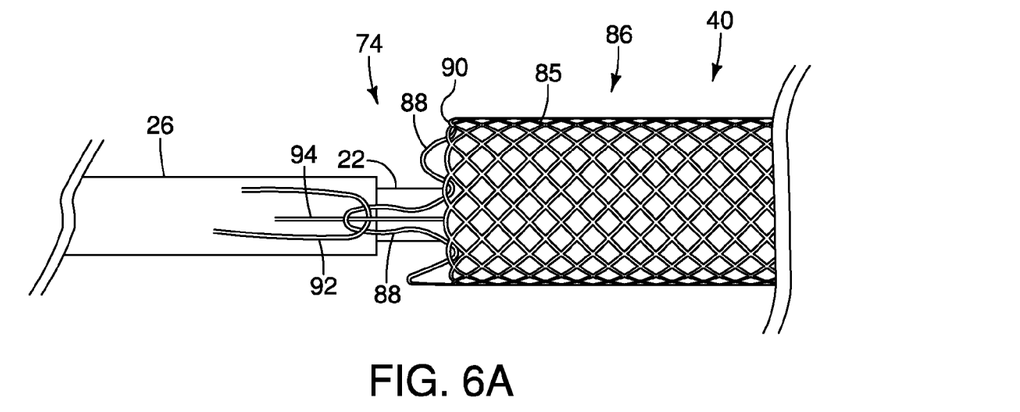
FIG. 6A is a partial side view of an embodiment of a proximal constraining member.
Figure 6B:
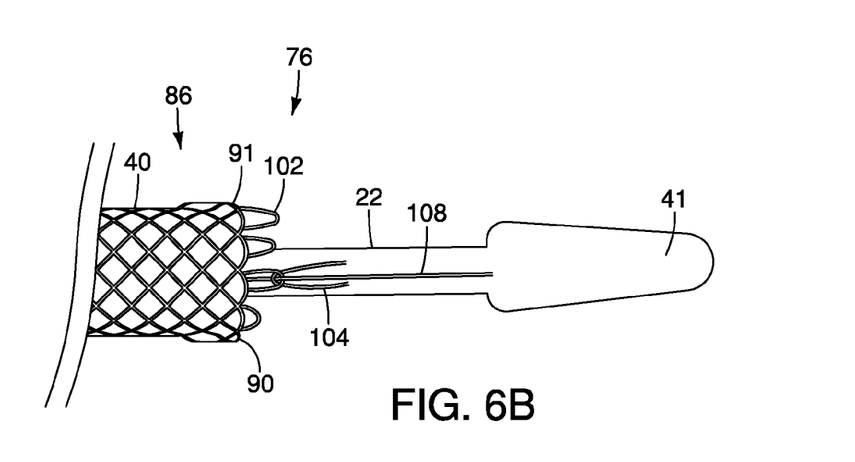
FIG. 6B is a partial side view of an embodiment of a distal constraining member.
Figure 6C:
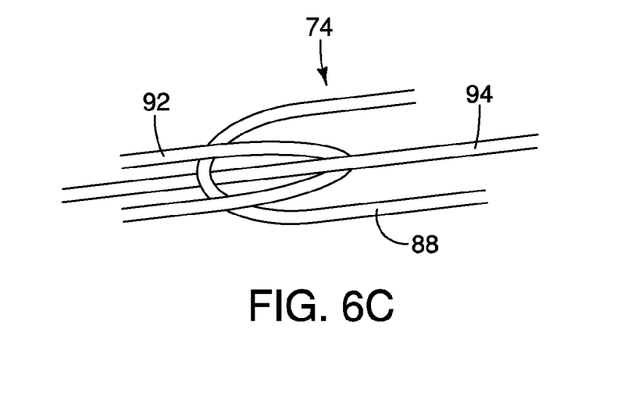
FIG. 6C is a partial enlarged view of the constraining member shown in FIG. 6A.

FIGS. 6A-6C illustrate an exemplary embodiment of the proximal constraining member 74 (FIG. 6A) and the first distal constraining member 76 (FIG. 6B). The second distal constraining member 78 is similar to the configuration of the first distal constraining member 76 and is not shown. An exploded view of the components of the proximal constraining member 74 is shown in FIG. 6C and the components of the first distal constraining member 76 may be a mirror image of the components of the proximal constraining member 74. As shown in FIG. 6A, a proximal end portion 85 of the bifurcated stent 40 remains connected to the outer shaft 26 even in the expanded configuration 86 using the proximal constraining member 74 in combination with the first and second distal constraining members 76, 78. The proximal constraining member 74 may include a first loop 88 that may be interwoven through one or more peaks 90 of the stent 40 so that the first loop 88 when pulled taught will collapse the peaks 90 of the stent 40 onto the inner shafts 22, 24. The proximal constraining member 74 may further include a second retaining loop 92 that may be attached to the outer shaft 26.

The proximal constraining member 74 may also include a proximal retaining wire 94 that is configured to cooperate with the first loop 88 and the second retaining loop 92 to releasably lock the first loop 88 to the second retaining loop 92 to allow selective expansion and contraction of the bifurcated stent 40 when the handle 30 is moved between the open position 84 and the closed position 80 in cooperation with the first and second distal constraining members 76, 78. The first loop 88, the second loop 92 or both may be anchored at one or more points to better secure the stent 40 over the inner shafts 22, 24, for example in a system 10 that is provided without a sheath. In some embodiments, the first loop 88 may be wound around the inner shafts 22, 24 or the outer shaft 26 to facilitate holding the stent to the inner shafts 22, 24 as the delivery system 10 is advanced to the treatment site through a curve, for example through an endoscope.

An exemplary cooperative configuration of the proximal constraining member 74 is shown in FIG. 6C where a portion of the first loop 88 and the second retaining loop 92 are overlapping and the proximal retaining wire 94 extends through the overlapping loops 88, 92 to releasably hold the two loops 88, 92 together. The proximal retaining wire 94 shown in FIG. 6A may be frictionally engaged with a portion of the outer shaft 26 to hold the proximal retaining wire 94 in position until the bifurcated stent 40 is in the proper position for release as discussed above. The proximal retaining wire 94 may be proximally withdrawn to release the proximal constraining member 74 and to completely release the stent 40 from connection to the inner shafts 22, 24 and the outer shaft 26.

As shown in FIG. 6B, a distal end portions 91 of the bifurcated stent 40 may remain connected the inner shafts 22, 24 even in the expanded configuration 86 using the first distal constraining member 76 and the second distal constraining member 78 (The second distal constraining member 78 may be similarly configured to the first constraining member and is not shown). The distal constraining members 76, 78 each may include a first loop 102 that may be interwoven through one or more peaks 90 of the bifurcated stent 40 so that the first loop 102 when pulled taught will collapse the peaks 90 of the stent 40 onto the inner shaft 22. The distal constraining members 76, 78 may further each include a second retaining loop 104 that may be attached to the inner shaft 22, 24, respectively. The first loop 102, the second loop 104 or both may be anchored at one or more points to better secure the stent 40 on the inner shafts 22, 24, for example in a system 10 that is provided without a sheath. In some embodiments, the first loop 102 may be wound around the inner shaft 22, 24 or the outer shaft 26 to facilitate holding the stent 40 to the inner shaft 22 as the delivery system 10 is advanced to the treatment site through a curve similar to the loop 88 described above.

The distal constraining members 76, 78 may also include each a distal retaining wire 108 that is configured to cooperate with the first loop 102 and the second retaining loop 104 to releasably hold the loops 102, 104 together to allow selective expansion and contraction of the stent 40 when the handle 30 is moved between the open position 84 and the closed position 80. The distal retaining wire 108 may be frictionally engaged with the inner shaft 22, 24 or a distal tip 41 to hold the distal retaining wire 108 in position until the bifurcated stent 40 is properly positioned for release. The distal constraining members 76, 78 may be configured similarly to the proximal constraining member 74 shown in FIG. 6C with the distal retaining wire 108 releasably locking the first loop 102 and the second retaining loop 104 together. Each distal retaining wire 108 may be proximally withdrawn to release the distal constraining member 76, 78 and to completely release the stent 40 from connection to the inner shafts 22, 24.

The proximal and distal retaining wires 94, 108 may be connected to the handle 30 for proximal withdrawal from the loops 88, 92, 102, 104. The withdrawal of the proximal and distal retaining wires 102, 104 may be simultaneous or sequential. Because the stent 40 has been positioned in the proper position within the lumen of the patient in the expanded configuration 86, the timing of the release of the retaining wires 94, 108 is not critical for the positioning of the stent 40. As will be understood by one skilled in the art, the connections between the proximal and distal constraining members and the inner and outer shafts may be configured in any arrangement that allows the inner and outer shafts to move relative to each other to cooperatively expand and constrain the stent. In embodiments provided without the outer sheath 32, the peaks 90 of the stent 40 are collapsed closely against the inner catheters 22, 24 at both ends of the stent 40 for delivery to the patient site.

While the proximal and distal restraining members 74, 76, 78 have been described with reference to connection to the proximal and distal end portions 85, 91 of the stent 40, it is also possible to provide proximal and distal constraining members 74, 76, 78 that are connected to other portions of the stent 40 and still provide a constrained configuration 60 for the stent 40. For example, the proximal constraining member may be connected to a mid proximal portion or mid-point of the stent and the distal constraining members may be connected to the distal end portions of the stent. Similarly, the proximal constraining member may be connected to the proximal end portion of the stent and the distal constraining members may be connected to the midpoint of mid distal portions of the stent or both the proximal and distal constraining members may be connected to other than the proximal and distal end portions of the stent. In some embodiments, the proximal or the distal constraining members or both proximal and distal constraining members may be connected to the stent at a plurality of positions on the stent.

Figure 7:
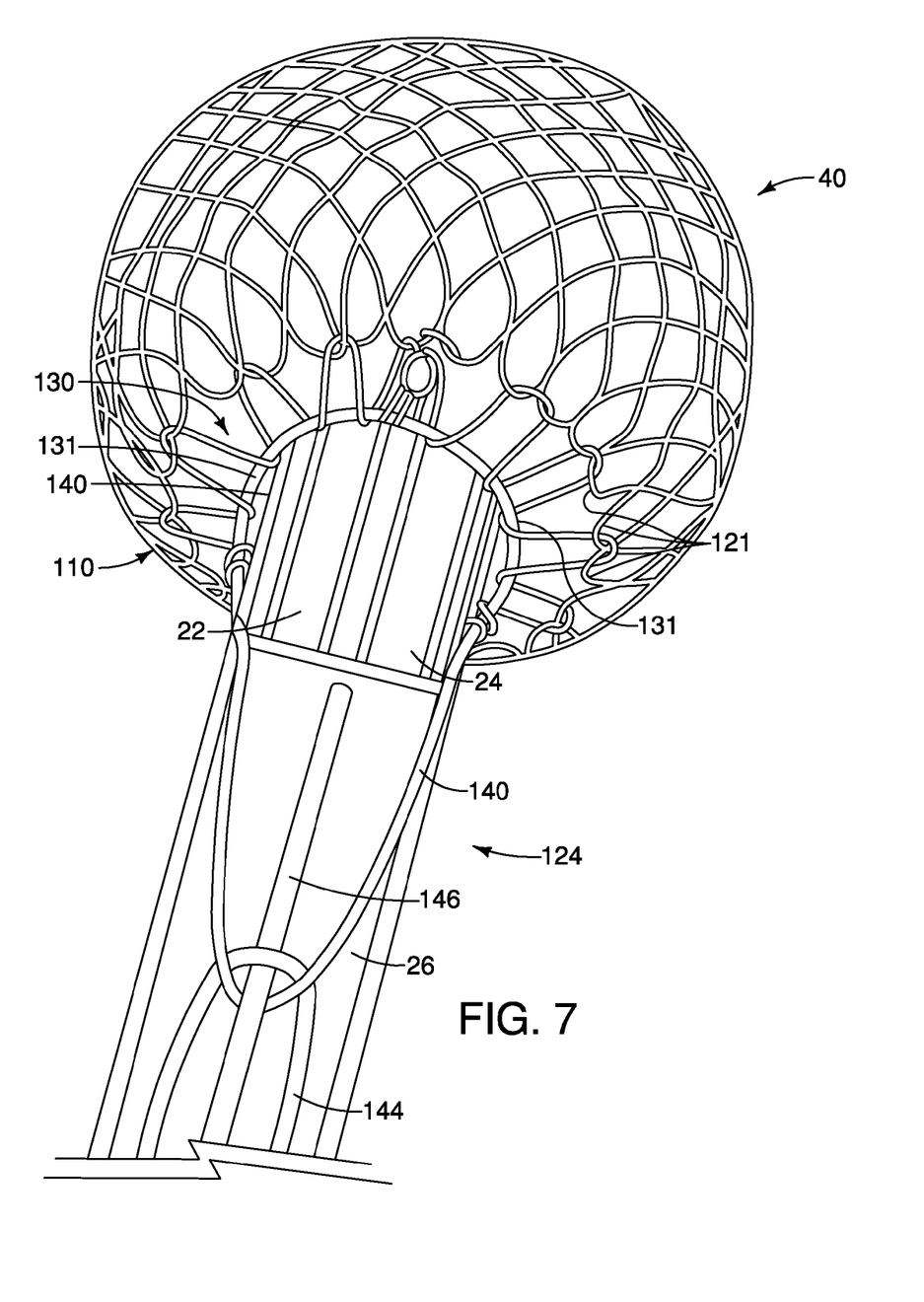
FIG. 7 is a partial perspective view of an alternative embodiment of a proximal constraining member.
Figure 8:
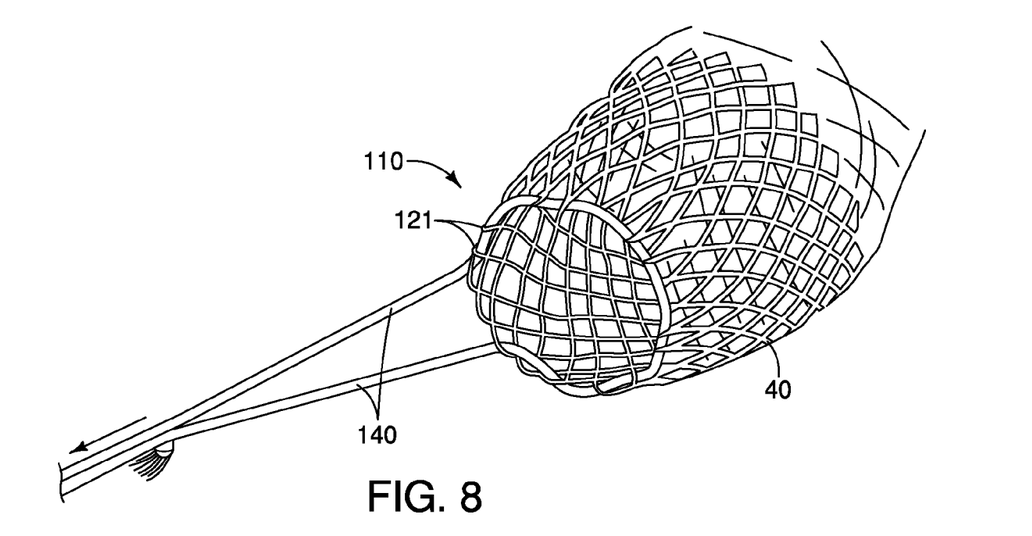
FIG. 8 is a perspective view of an alternative embodiment of a constraining member.

Another exemplary embodiment of a proximal constraining member 124 is illustrated in FIG. 7. The proximal constraining member 124 is connected to the outer shaft 26. Distal constraining members connected to the inner shaft 22 and the inner shaft 24 may be similarly configured to the proximal constraining member 124 and are not shown.

The proximal constraining member 124 may include an outer filament 130 and an inner filament 140. The outer filament 130 may be interwoven through one or more peaks 121 at an end portion 110 of the stent 40. The inner filament 140 engages with the outer filament 130 to pull the outer filament 130 taught and to reduce the diameter of the stent end portion 110 and collapse stent 40. The proximal constraining member 124 may further include a retaining loop 144 that may be attached to the outer shaft 26. The proximal constraining member 124 may also include a proximal retaining wire 146 that is configured to cooperate with the inner filament 140 and the retaining loop 144 to releasably lock the inner filament 140 to the retaining loop 144 to allow selective expansion and contraction of the stent 40 when the inner and outer shafts 22, 24, 26 are longitudinally moved relative to each other constrain and unconstrain the stent 40.

FIG. 7 illustrates the proximal constraining member 124 where a portion of the inner filament 140 and the retaining loop 144 are overlapping and the proximal retaining wire 146 extends through the overlapping loops of the inner filament 140 and the retaining loop 146 to releasably hold the two loops 140, 146 together. The proximal retaining wire 146 shown in FIG. 7 may be frictionally engaged with a portion of the outer shaft 26 to hold the proximal retaining wire 146 in position until the bifurcated stent 40 is in the proper position for release as discussed above. The proximal retaining wire 146 may be proximally withdrawn to release the proximal constraining member 124 and to completely release the stent 40 from connection to the outer shaft 26.

In some embodiments, the stent delivery system 10 may be provided with proximal and distal constraining members 74, 76, 78 having the outer filament 140 woven through the peaks 121 at the end portion 110 of the stent 40 without the inner filament. The outer filament 140 is shown woven though the peaks 121 in FIG. 8. The outer filament 140 may be connected to a proximal or distal loop 144 and cooperatively connected to the inner or outer shaft 22, 24, 26 by the retaining wire 146 as described above with reference to FIG. 7.

Figure 9:
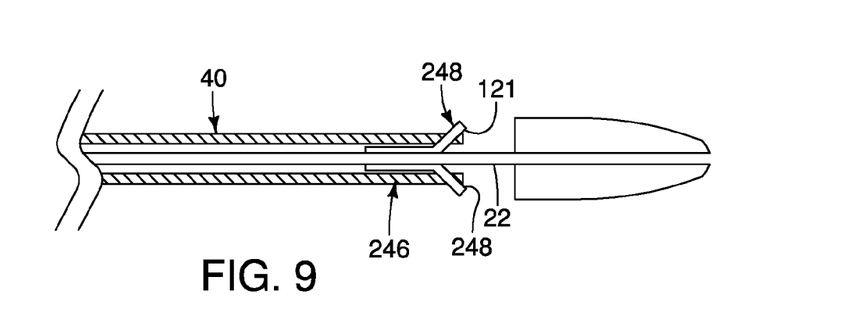
FIG. 9 is a partial side view of an alternative embodiment of a distal constraining member.
Figure 10:
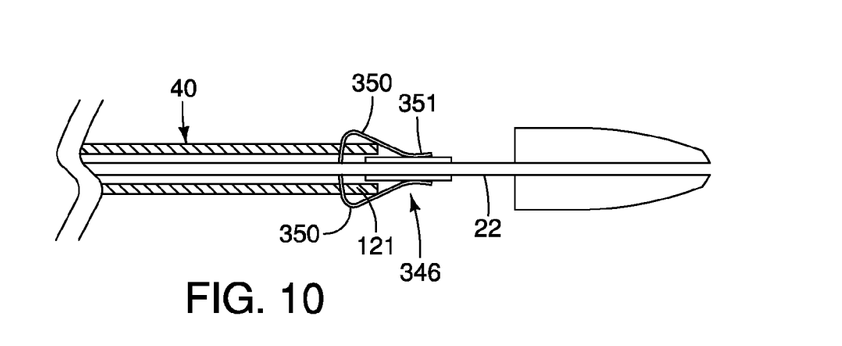
FIG. 10 is a partial side view of an alternative embodiment of a distal constraining member.

Additional configurations for the proximal and distal constraining members are also possible. By way of non-limiting example, additional configurations for alternative embodiments of the constraining members are shown in FIGS. 9 and 10. A similar proximal constraining member and second distal constraining member are also provided, but not shown. The proximal and first and second distal constraining members may be the same or different. The distal constraining member 246 shown in FIG. 9 includes one or more hooks 248 that may hook onto peaks 121 of the stent 40 to constrain the stent 40 on the inner shaft 22. A plurality of hooks 248 may be provided on the inner shaft 22 and spaced apart to evenly hold the stent 40 in position. For example, 4 hooks may be provided and spaced apart by 90°. The hooks 248 may also be skived from the inner shaft 22. Other combinations of numbers of hooks and spacing of the hooks may also be provided, including uneven spacing and uneven numbers of hooks. One or more hooks 248 may be provided with a retaining wire 288 (not shown) extending through the hook 248 and the stent peak 121 to releasably lock the stent 28 to the delivery system 10, for example, similar to the embodiment described above with reference to FIGS. 6A-6C.

The distal constraining member 246 may also include a loop (not shown) similar to the loop 88 described in FIG. 6A above that is woven between the peaks 121 and the hook 248 connects to the loop 88 to constrain the stent 40. The hook 248 may be released from the stent peak 121 or the loop 88 by moving the inner shafts 22, 24 relative to the outer shaft 26 so that the constraining members move closer together so that the stent 40 expands and releases the hooks 248. The hooks 248 may also be released by withdrawing the retaining wire 288 and releasing the lock between the peak 121 and the hook 248, for example. The stent 40 may be expanded and constrained a plurality of times prior to release of the retaining wire 288 similar to the embodiments described above.

FIG. 10 illustrates the first distal constraining member 346 that includes one or more grasping members 350 that grasp a portion of a stent 40 to hold the stent on the inner shaft 22. The grasping members 350 may be provided on the inner shaft 22 and spaced apart to hold the stent 40 in position similar to the arrangements described above for the hooks 228. One or more grasping members 350 may be provided with a retaining wire 388 (not shown) extending through the grasping member 350 and the stent 40 to releasably lock the stent 40 to the delivery system 10 similar to the embodiments described above. The distal constraining member 346 may also include a loop 382 (not shown) similar to the loop 88 described above that is woven between the peaks 121 of the stent 40 and the grasping member 350 connects to the loop 382 to hold the stent 40 while the inner and outer shafts 22, 24, 26 are longitudinally moved relative to each other to hold the stent in the constrained configuration 60. The grasping member 350 may be released from the stent 40 or the loop 382 by opening the grasping member 350 away from the stent 40 after the torsional force has been released, for example by pressing on a distal portion 351 of the grasping member 350 to flex the grasping member 350 open. The stent 40 may be expanded and constrained a plurality of times prior to release of the retaining wire 388 similar to the embodiments described above. Additional configurations for proximal and first and second distal constraining members are also possible.

Figure 11:
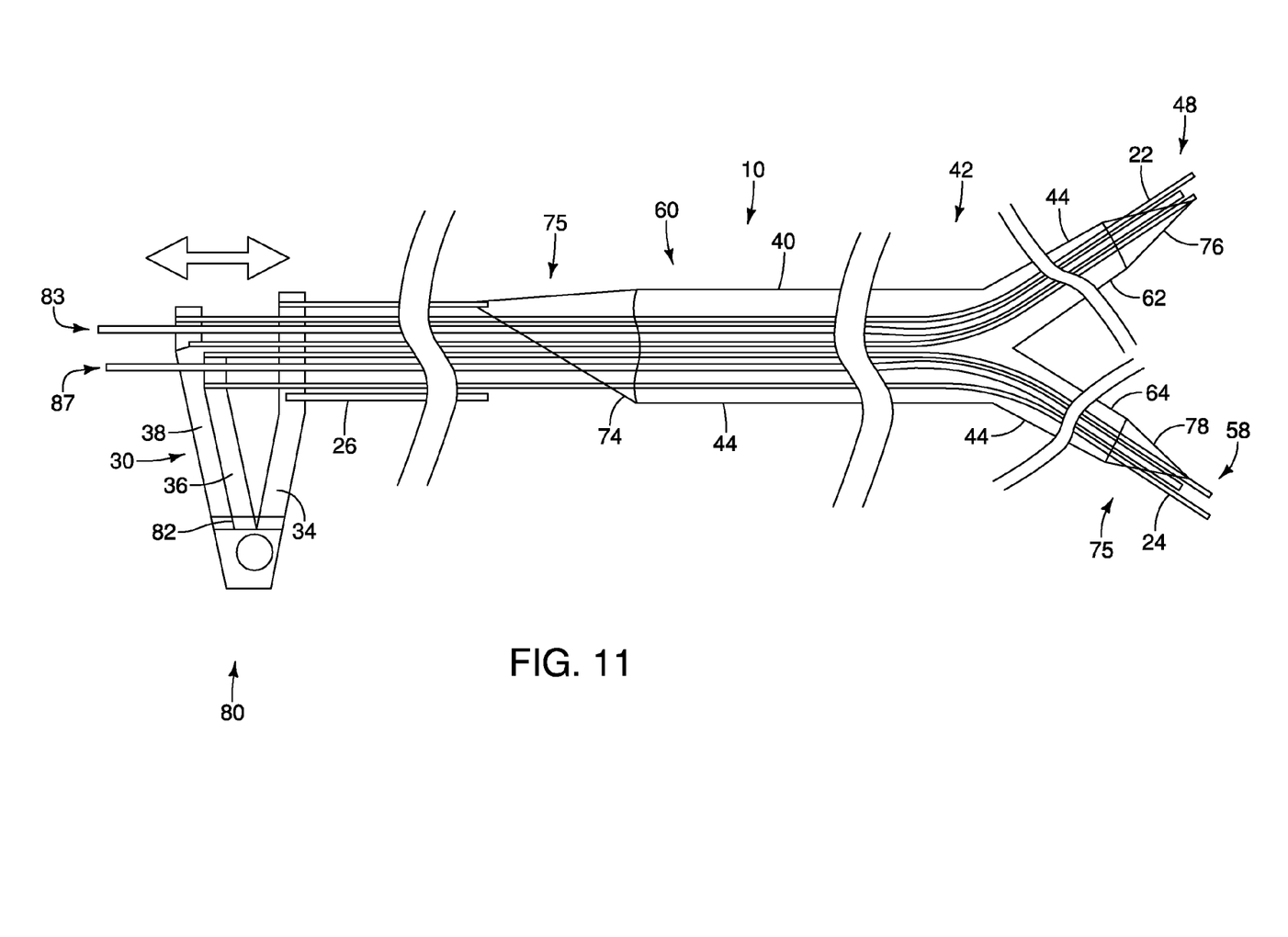
FIG. 11 is a sectional view of a delivery system illustrating stiffening members.

In some embodiments, a first stiffening member 83 may be removably provided in the inner shaft 22 and a second stiffening member 87 may be removably provided in the inner shaft 24 as shown in FIG. 11. The stiffening members may be provided as a mandrel, catheter, rod and the like that is removably insertable into the inner shafts 22, 24. The stiffening members 83, 87 may be provided to help increase the rigidity of the inner shafts 22, 24 against the inward tensioning force of the stent 40 when the stent 40 is in the constrained configuration 60. In some embodiments, the inner shafts 22, 24 may be provided in a soft material to facilitate passage through the body lumen. In the event that the materials are sufficiently soft, the inner shaft 22 may collapse or deform in response to the tensioning force of the stent 40 provided by the proximal and distal constraining members 74, 76, 48 longitudinally constraining the stent 40 against the inner shafts 22, 24. The stiffening members 83, 87 may be made from any material having suitable stiffness to provide support for the inner shafts 22, 24 with the stent 40 longitudinally tensioned thereon. Exemplary materials for forming the shaft include, but are not limited to, metal alloys such as stainless steel, tantalum or its alloys, tungsten, platinum, gold, copper, palladium, rhodium, or a superelastic alloys, such as nitinol or polymers that can be provided with sufficient shore hardness, such as Pebax, Peek, polyimide, liquid crystal polymers (LCP) such as Vectran, polyethylene, polyethylene terephthalate and Nylon. As shown in FIG. 2, the outer sheath 70 may be provided for delivery of the stent to the area of the treatment site. The outer sheath 72 may provide some compression of the stent 40 against the inner shafts 22, 24 for delivery of the device 10 to the treatment site with the stiffening members 83, 87 removed and the stent 40 in the constrained configuration 60. (See FIG. 1.) The stiffening members 83, 87 may be inserted into the inner shafts 22, 24 when the stent 40 is near the proper position for implantation into the patient and the outer sheath 70 is over the stent 40 as shown in FIG. 2. The outer sheath 70 may be withdrawn and the stent 40 remains constrained on the inner shafts 22, 24 by the proximal and distal constraining members 74, 76, 78. The stiffening members 83, 87 support the inner shafts 22, 24, respectively against the compressive tensioning force exerted by the proximal and distal constraining members 74, 76, 78.

The materials used to manufacture the components of the stent delivery systems described herein may be any materials known to one skilled in the art that are suitable for use in patients. By way of non-limiting example, the shafts and sheaths may be formed from polytetrafluoroethylene (PTFE) particularly when a low friction outer sheath is desirable. Nylon and HDPE may also be used for clarity. Additional possible materials include, but are not limited to the following, polyethylene ether ketone (PEEK), fluorinated ethylene propylene (FEP), perfluoroalkoxy polymer resin (PFA), polyamide, polyurethane, high density or low density polyethylene, and nylon including multi-layer or single layer structures and the like and may also include reinforcement wires, braid wires, coils, coil springs and or filaments. The stent may be formed from but is not limited to the following materials: Nickel titanium alloys, for example, nitinol, stainless steel, cobalt alloys and titanium alloys. The loops of the constraining members may be made from common suture material as known in the art, for example polyester suture such as 4-0 Tevdek®, nylon, silk, polypropylene, ultra high molecular weight polyethylene (UHMPE) and the like. The sutures may be monofilament, braided, twisted or multifilament. The loops and the retaining wires may also be made from a metallic alloy such as stainless steel or nickel titanium. In some embodiments, the stent, the loops and/or the retaining wires may be made from biodegradable materials. A number of bioabsorbable homopolymers, copolymers, or blends of bioabsorbable polymers are known in the medical arts. These include, but are not necessarily limited to, polyesters including poly-alpha hydroxy and poly-beta hydroxy polyesters, polycaprolactone, polyglycolic acid, polyetheresters, poly(p-dioxanone), polyoxaesters; polyphosphazenes; polyanhydrides; polycarbonates including polytrimethylene carbonate and poly(iminocarbonate); polyesteramides; polyurethanes; polyisocyantes; polyphosphazines; polyethers including polyglycols polyorthoesters; expoxy polymers including polyethylene oxide; polysaccharides including cellulose, chitin, dextran, starch, hydroxyethyl starch, polygluconate, hyaluronic acid; polyamides including polyamino acids, polyester-amides, polyglutamic acid, poly-lysine, gelatin, fibrin, fibrinogen, casein, collagen.

Other suitable biocompatible materials may also be used for any of the components described herein.

Operation of the stent delivery systems of the present invention is described with reference to the stent delivery system 10 by way of non-limiting example. Alternative methods of operating the system may also be used. The stent delivery system 10 may be provided in a sterile packaging. In some embodiments, the stent 40 may be provided in the expanded configuration 86 or constrained configuration 60 within the packaging. For example, some stent materials may weaken or otherwise deform when stored in a constrained configuration 60 with the longitudinal tension exerting force on the stent during shipping and storage. In some embodiments provided with an outer sheath 70, the outer sheath 70 may be provided to hold the stent 40 in position on the delivery system 10 without having the proximal and distal constraining members 74, 76, 78 tensioning the stent 40. For example, the system 10 may be provided with the handle 30 in the open position 84 and the outer sheath 70 over the stent 4 on the inner shafts 22, 24. Prior to insertion of the system 10 into the patient, the operator may move the handle 30 to the closed position 80 and place longitudinal tension on the stent 40 using the proximal and distal constraining members 74, 76, 78 to constrain the stent 40 against the inner shafts 22, 24. The stent 40 may be provided in the expanded configuration 86 in the absence of a sheath as well and be moved to the constrained configuration 60 by operation of the handle 30 to the closed position 84 prior to delivery to the patient.

The endoscope is positioned within the lumen so the operator can view the proximal side of the stricture. The guidewires 46, 56 are inserted through the stricture and the endoscope is removed. The operator inserts a distal portion 31 of the stent delivery system 10 into the patient's lumen with the stent 40 in the constrained configuration 60. The guidewire 46, 56 may be inserted first to navigate a tortuous pathway to the treatment site and the system 10 is delivered over the guidewire 46, 56 to the treatment site. The endoscope may then be placed into the patient's lumen adjacent and parallel to the system 10. Alternatively, the stent delivery system 10 may be inserted into the patient's lumen through the working channel of an endoscope, depending on the size and location of the lumen.

A viewing port of the endoscope is used to identify the branch at which the stricture is positioned. The stent 40 is positioned near the stricture at the bifurcation. For embodiments having softer inner shafts 22, 24, the stiffening members 83, 87 are inserted through the inner shafts 22, 24 to provide support for the longitudinally tensioned stent 40. The outer sheath 70, if present, is proximally withdrawn and the stent 40 in the constrained configuration 60 is exposed within the patient's lumen. The first stent arm 62 and the second stent arm 64 are allowed to separate by releasing some tension by moving the one or both inner shafts 22, 24 relative to the outer shaft 26. The first and second stent arms 62, 64 may be expanded separately or together by moving the first inner shaft 22 separate from or together with the second inner shaft 24 in relation to the outer shaft 26. The stent 40 may be moved within the main lumen and the bifurcation lumens to correctly position the stent 40 at the treatment site. The stent 40 is moved to the fully expanded configuration 86 by movement of the handle 30 to the open position 84 that moves the proximal and distal constraining members 74, 76, 78 to the second position 79 releasing the longitudinal tension on the stent 40. The position of the expanded stent 40 is monitored using the endoscope. The stent 40 may be returned to the constrained configuration 60 by the operator moving the handle 30 to the closed position 30 and returning the proximal and distal constraining members 74, 76, 78 to the first position 75 to longitudinally tension the stent 40 against the inner shafts 22, 24 for example if the stent 40 is incorrectly positioned. The stent 40 may be moved from the constrained configuration 60 to the expanded configuration 86 as many times as needed.

Once the proper position for the stent 40 is achieved within the patient's bifurcated stricture, the proximal and distal retaining wires 94, 108 may be proximally withdrawn from the stent 40 to completely release the stent 40 from the delivery system 10. The delivery system 10 is withdrawn proximally from the patient and the endoscope removed.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A stent delivery system comprising:
   a first elongate shaft including a proximal portion, a distal portion, and a lumen extending at least partially therethrough;
   a second elongate shaft including a proximal portion, a distal portion, and a lumen extending at least partially therethrough, the second elongate shaft longitudinally movable relative to the first elongate shaft;
   a bifurcated stent having a first arm positioned on the distal portion of the first elongate shaft, a second arm positioned on the distal portion of the second elongate shaft, and a main body positioned on the first and second elongate shafts, the stent having a constrained configuration and an expanded configuration;
   a proximal constraining member releasably connected to a proximal portion of the stent, the proximal constraining member comprising a proximal retaining wire releasably extending through first and second proximal loops, the proximal constraining member having a first position and a second position;
   a first distal constraining member releasably connected to the first arm of the stent, the first distal constraining member comprising a first distal retaining wire releasably extending through a first distal loop, the first distal constraining member having a first position and a second position; and
   a second distal constraining member releasably connected to the second arm of the stent, the second distal constraining member comprising a second distal retaining wire releasably extending through a second distal, the second distal constraining member having a first position and a second position;
   wherein the proximal constraining member and the first and second distal constraining members are configured to cooperatively apply a longitudinal tensile force to at least a portion of the stent in the constrained configuration with the proximal and first and second distal constraining members each in the first position.

2. The stent delivery system of claim 1, further comprising an elongate outer shaft longitudinally movable relative to the first and second elongate shafts.

3. The stent delivery system of claim 1, further comprising a handle operably connected to the proximal and first and second distal constraining members for moving the proximal and first and second distal constraining members between the first position and the second position to move the stent between the constrained configuration and the expanded configuration.

4. The stent delivery system of claim 1, wherein the proximal and the first and second distal retaining wires are removable from connection with the stent to completely release the stent from the delivery system.

5. The stent delivery system of claim 1, wherein the stent is repeatedly movable between the constrained configuration and the expanded configuration.

6. The stent delivery system of claim 1, wherein the first distal constraining member is connected to the first elongate shaft and the second distal constraining member is connected to the second elongate shaft.

7. The stent delivery system of claim 6, wherein the proximal constraining member is connected to an elongate outer shaft movably positionable over a portion of the first and second elongate shafts.

8. The stent delivery system of claim 1, wherein the first distal constraining member is movable to the second position with the second distal constraining member in the first position.

9. The stent delivery system of claim 1, further comprising a stiffening member removably positionable in the first or the second lumen to support the elongate shaft against the longitudinal force applied to the stent.

10. The stent delivery system of claim 1, further comprising a sheath removably positionable over the stent.

11. The stent delivery system of claim 1, wherein the retaining wire releasably connects the proximal loops together.

12. The stent delivery system of claim 1, wherein the first distal loop is interwoven through a plurality of peaks of the first arm of the stent.

* * * * *

UNITED STATES PATENT AND TRADEMARK OFFICE
CERTIFICATE OF CORRECTION

PATENT NO. : 8,709,063 B2
APPLICATION NO. : 13/160640
DATED : April 29, 2014
INVENTOR(S) : Vincent McHugo It is certified that error appears in the above-identified patent and that said Letters Patent is hereby corrected as shown below:

In the Claims

In column 12, claim 1, line 13, after "through a second" replace "distal," with --distal loop,--.

Signed and Sealed this
Twelfth Day of April, 2016

Michelle K. Lee
*Director of the United States Patent and Trademark Office*